United States Patent [19]

Honda et al.

[11] Patent Number: 4,476,310

[45] Date of Patent: Oct. 9, 1984

[54] PROCESS FOR THE PREPARATION OF INDOLES

[75] Inventors: Tadatoshi Honda, Hiratsuka; Fujio Matsuda; Tadamitsu Kiyoura, both of Kamakura; Kazuhiro Terada, Yokohama, all of Japan

[73] Assignee: Mitsui Toatsu Chemicals, Inc., Tokyo, Japan

[21] Appl. No.: 386,651

[22] Filed: Jun. 9, 1982

[30] Foreign Application Priority Data

Jun. 12, 1981 [JP] Japan ................................. 57-89612

[51] Int. Cl.$^3$ .................. C07D 209/04; C07D 209/12
[52] U.S. Cl. .................................... 548/508; 548/469; 548/509
[58] Field of Search ......................................... 548/508

[56] References Cited

FOREIGN PATENT DOCUMENTS

| 0105663 | 8/1980 | Japan | 548/508 |
|---|---|---|---|
| 36451 | 4/1981 | Japan . | |
| 0150062 | 11/1981 | Japan | 548/508 |

*Primary Examiner*—Paul M. Coughlan, Jr.
*Assistant Examiner*—David B. Springer
*Attorney, Agent, or Firm*—Fisher, Christen & Sabol

[57] ABSTRACT

A process for the preparation of indoles which comprises reacting aniline or a derivative thereof with a 1,2-glycol in the presence of a catalyst comprising silver supported on a carrier having a specific surface area of not less than 10 m$^2$/g.

6 Claims, No Drawings

PROCESS FOR THE PREPARATION OF INDOLES

BACKGROUND OF THE INVENTION

1. Field of the Invention

This invention relates to a process for the preparation of indoles by reacting aniline or a derivative thereof with a 1,2-glycol in the presence of an improved catalyst.

2. Description of the Prior Art

In the past, the present inventors discovered that indoles can be directly prepared in a single step through the reaction of aniline or a derivative thereof with a 1,2-glycol and that certain catalysts are useful in promoting this reaction. Several processes based on these discoveries have already been disclosed. Moreover, another process for the preparation of indoles by contacting aniline or a derivative thereof with ethylene glycol in the vapor phase is disclosed in Japanese Patent Laid-Open No. 36451/'81. This process is characterized in that the vapor phase reaction is carried out in the presence of a catalyst which is commonly used for the dehydrogenation of alcohols.

The present inventors have made further investigation and examination of such catalysts and have now found that a specific type of silver catalyst serves as a very excellent catalyst for the above-described reaction.

SUMMARY OF THE INVENTION

It is an object of the present invention to provide a process for the preparation of indoles in which a good yield of product can be obtained by reacting aniline or a derivative thereof with a 1,2-glycol in the presence of a catalyst having high activity.

According to the present invention, there is provided a process for the preparation of indoles, which comprises reacting aniline or a derivative thereof with a 1,2-glycol in the presence of a catalyst comprising silver supported on a carrier having a specific surface area of not less than 10 $m^2/g$.

DETAILED DESCRIPTION OF THE INVENTION

It is stated in Japanese Patent Laid-Open No. 36451/'81 that the catalysts commonly used for the dehydrogenation of alcohols are effective in the preparation of indoles by contacting aniline or a derivative thereof with ethylene glycol in the vapor phase. However, the findings obtained by the present inventors indicate that, by way of example, the Zn-Fe catalyst described at page 75 of "List of Catalysts Classified by Reaction" (published on Sept. 1, 1971 by Kagaku Kogyosha) is active for the dehydrogenation of cyclohexanol, but utterly inactive for the synthesis of indole from aniline and ethylene glycol.

As for silver catalysts, a number of catalysts for the synthesis of aldehydes by oxidative dehydrogenation of alcohols and for the synthesis of ethylene oxide by oxidation of ethylene are well known in the prior art. Among these silver catalysts, the catalysts for the oxidative dehydrogenation of alcohols consist of metallic silver itself, as described at pages 74 and 75 of the above-mentioned "List of Catalysts Classified by Reaction". On the other hand, the catalysts for the oxidation of ethylene consist of silver supported on a carrier having a specific surface area of not greater than 3 $m^2/g$ and typically not greater than 1 $m^2/g$, as described at pages 387 to 393 of "Practical Catalysts Classified by Reaction" (published on Dec. 25, 1970 by Kagaku Kogyosha).

These silver catalysts have been found to be scarcely active for the reaction of the present invention. However, a new class of catalysts which is very different from the above-described silver catalysts and has never been used in the prior art (e.g., a catalyst consisting of silver supported on an $SiO_2$-MgO carrier having a specific surface area of 170 $m^2/g$) can exhibit high activity for the reaction of the present invention.

The catalyst used in the process of the present invention comprises silver supported on a carrier having a specific surface area of not less than 10 $m^2/g$, preferably not less than 50 $m^2/g$, and more preferably not less than 100 $m^2/g$. This catalyst preferably contains silver in an amount of 0.1 to 50 parts by weight and more preferably 1 to 20 parts by weight per 100 parts by weight of the carrier.

Although a large number of carriers meeting the above-described requirement are known, it is preferable to use an oxide of at least one element selected from the group consisting of Si, Al, B, Sb, Bi, Sn, Pb, Ga, In, Ti, Zr, Be, Mg, Ca, Sr, Y, Zn, Cd, and the lanthanides, or activated carbon. Among these carriers, $SiO_2$-ZnO, $SiO_2$-CdO, $SiO_2$-MgO, $SiO_2$-$SrO_2$, $SiO_2$-$In_2O_3$, $SiO_2$-CaO, $SiO_2$, and activated carbon are particularly preferred.

When the oxidative dehydrogenation of alcohols is carried out in the presence of a silver catalyst within the scope of the present invention (i.e., a catalyst consisting essentially of silver supported on a carrier having a sufficiently large specific surface area), no aldehyde can be obtained, as evidenced by Reference Example 1 which will be given later. Accordingly, it is believed that the silver catalyst used in the process of the present invention is quite different in kind from the prior art catalysts commonly used for the dehydrogenation of alcohols.

In the above-described carriers of the $SiO_2$ type, the weight ratio of $SiO_2$ to the other oxide or oxides preferably ranges from 1:0.01 to 1:1 and more preferably from 1:0.05 to 1:0.2.

These carriers can be prepared, for example, by the following procedure: An aqueous solution of sodium silicate is mixed with an aqueous solution of a soluble salt of another constituent element (e.g., cadmium nitrate, zinc nitrate, magnesium chloride, strontium nitrate, or the like). To this mixture is added an acid or alkali according to the need. The precipitate so formed is thoroughly washed with water, dried, calcined in air at a temperature of 400° to 800° C. for a period of 2 to 4 hours, and then crushed or pelletized to form a carrier.

In these carriers, the specific surface area may vary widely according to the method of preparation. However, they usually have a specific surface area of 50 to 400 $m^2/g$. These carriers may further contain one or more additional oxides selected from oxides of Be, Mg, Ca, Sr, Ba, B, Al, Ga, In, Tl, Sc, Y, Co, Fe, Ni, Li, Na, K, Rb, Cs, and the lanthanides.

In addition, various types of activated carbon can be used as carriers. They include, for example, products made from coconut shell, wood, sawdust, lignin, coal, blood charcoal, bone charcoal, petroleum carbon, and the like. These products are available in powdered form, in crushed form, and in shaped form (e.g., in the shape of globules or cylinders).

Any conventional procedure may be used to support silver on the above-described carriers. By way of example, a catalyst can be prepared by soaking a carrier in an aqueous solution of silver nitrate, drying the carrier, and then heating it in a stream of hydrogen gas at a temperature of approximately 150° C. to reduce the silver nitrate.

In order to maintain the activity of the catalyst, suppress the occurrence of side reactions, and/or prevent the deposition of carbon on the catalyst surfaces, the catalyst of the present invention may further contain one or more additional components selected from IIa group elements (Be, Mg, Ca, Sr, and Ba), IIIa group elements (B, Al, Ga, In, and Tl), IIIb group elements (Sc, Y, and the lanthanides), VIII group elements (Fe, Co, Ni, and the platinum metals), and Ia group elements (Li, Na, K, Rb, and Cs).

The term "aniline or a derivative thereof" as used herein denotes a compound of the general formula

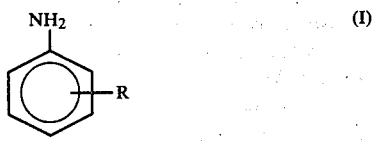

where R represents a hydrogen atom, a halogen atom, a hydroxyl group, an alkyl group, or an alkoxy group. Specific examples thereof include aniline, o-toluidine, m-toluidine, p-toluidine, o-haloanilines, p-haloanilines, m-haloanilines, o-aminophenol, m-aminophenol, p-aminophenol, o-anisidine, m-anisidine, p-anisidine, and the like.

The 1,2-glycol used in the process of the present invention is a compound selected from ethylene glycol, propylene glycol, 1,2-butanediol, 1,2,4-butanetriol, glycerol, 2,3-butanediol, diethylene glycol, and the like.

Although the process of the present invention can be carried out in the vapor phase, the liquid phase, or a mixture vapor-liquid phase, it is usually carried out in the vapor phase. Where the process of the present invention carried out in the vapor phase, a fixed-bed, fluidized-bed, or moving-bed reactor can be used to effect the reaction by heating the vapors of aniline or a derivative thereof and a 1,2-glycol in the presence of a catalyst. In this case, various inert gaseous substances may coexist as diluents for the vapors of the starting materials. Useful inert gaseous substances include, for example, nitrogen gas, carbon dioxide gas, water vapor, and the vapors of compounds that are inert to this reaction. Moreover, hydrogen gas may also be used as a diluent.

The use of hydrogen gas is particularly suitable for the purpose of maintaining the activity of the catalyst.

Similarly, the use of water vapor is suitable for the purposes of maintaining the activity of the catalyst and enhancing the yield of the desired product, because it can suppress the decomposition of the 1,2-glycol over the catalyst.

The amounts of starting materials fed to the reactor should be such that 0.01 to 5 moles and preferably 0.05 to 2 moles of the 1,2-glycol is provided for each mole of the aniline or derivative thereof. If the amounts are outside this range, a reduction in yield will be caused and/or large amounts of by-products will be formed. These starting materials are fed, after being vaporized in advance or directly in liquid form, to the reactor at a liquid space velocity of 0.01 to 5 liters per liter of the catalyst per hour.

The process of the present invention is carried out at a reaction temperature in the range of 200° to 600° C., preferably 250° to 500° C., and more preferably 300° to 400° C. If the reaction temperature is lower than 200° C., the reaction can hardly proceed, while if it is higher than 600° C., undesirably large amounts of by-products will be formed.

The reaction pressure may be superatmospheric, atmospheric, or subatmospheric.

Where the process of the present invention is carried out in the liquid phase or in a mixed vapor-liquid phase, the reaction is effected by heating a mixture of aniline or a derivative thereof and a 1,2-glycol in the presence of a catalyst as defined above. In this case, various inert gaseous substances and/or solvents may coexist as diluents for the starting materials. Useful inert gaseous substances include, for example, nitrogen gas, carbon dioxide gas, water vapor, and the vapors of compounds that are inert to this reaction. Useful solvents include, for example, benzene, xylene, toluene, methanol, ethanol, isopropanol, dioxane, dimethylformamide, dimethyl sulfoxide, pyridine, N-methylpyrrolidone, trimethylamine, diethylamine, triethylamine, tripropylamine, tributylamine, diphenylamine, triphenylamine, and other organic solvents.

In the case of liquid phase reaction, the process of the present invention can be carried out in a fixed-bed, fluidized-bed, or moving-bed reactor or in a rotary or continuous reactor for liquid phase reactions. However, no particular limitation is placed on the type of reactor used.

The amounts of starting materials used for this reaction should be such that 0.05 to 1 mole and preferably 0.1 to 2 moles of the 1,2-glycol is provided for each mole of the aniline or derivative thereof.

No particular limitation is placed on the amount of catalyst for this reaction. However, the catalyst is generally used in such an amount as to provide 0.01 to 20 g and preferably 0.1 to 10 g of the active component thereof for each mole of the aniline or derivative thereof.

The reaction temperature should be in the range of 200° to 500° C. and preferably 250° to 400° C. If the reaction temperature is lower than 200° C., the reaction can hardly proceed, while if it is higher than 500° C., undesirably large amounts of by-products will be formed.

The reaction pressure may be superatmospheric or atmospheric.

In various embodiments of the present invention, the desired indole can readily be obtained in pure form by isolating it from the reaction product according to any conventional technique such as distillation.

The present invention is further illustrated by the following examples.

EXAMPLE 1

A solution was prepared by dissolving 30 g of cadmium nitrate and 19 g of 60% nitric acid in 300 ml of water, and then added to a solution of 130 g of No. 3 water glass (containing 29% of $SiO_2$ and 9% of $Na_2O$) in 2,000 ml of water. The precipitate so formed was thoroughly washed with water, dried at 150° C., and then calcined in air at 500° C. for 3 hours. The resulting $SiO_2$-CdO (in a weight ratio of 3:1) was crushed and sieved to obtain a carrier having a particle size of 10–28 mesh (and hence a specific surface area of 240 m²/g). This carrier was soaked in a 25 wt. % aqueous solution of silver nitrate, dried at 80° C., and then heated in a stream of hydrogen gas at 150° C. for 2 hours to reduce the silver nitrate and thereby form a catalyst. A Pyrex glass flow reactor having an internal diameter of 10 mm was packed with 5 ml of this catalyst. The front end of this reactor was connected to a feed inlet pipe and a gas inlet pipe to establish a feed vaporization zone, while the rear end thereof was connected to a receiver by way of an air-cooling zone.

In the reaction zone, the internal temperature of the reactor was kept at 325° C. Then, a mixture consisting of 7 moles of aniline and 1 mole of ethylene glycol was introduced thereinto through the feed inlet pipe at a liquid space velocity of 0.3 liter per liter of the catalyst per hour. At the same time, nitrogen gas at atmospheric pressure was passed therethrough in an amount of 10 moles per mole of the aniline used as a starting material. The reaction was carried out for 27 hours, during which time samples of the reaction mixture were collected for 2-hour period between 1 and 3 hours after the start of the reaction and for a 2-hour period between 25 and 27 hours after the start of the reaction (i.e., a period in which the activity of the catalyst was stabilized). The samples collected during the former and the latter period were called reaction mixtures A and B, respectively. Gas-chromatographic analysis revealed that the yield of indole based on the ethylene glycol was 63% for reaction mixture A and 52% for reaction mixture B.

EXAMPLE 2

The procedure of Example 1 was repeated except that the nitrogen gas was replaced by each of the gases indicated in Table 1. The results thus obtained are summarized in Table 1.

TABLE 1

| Run No. | Gas used Type | Molar ratio | Yield of indole (%) Reaction mixture A | Reaction mixture B |
|---|---|---|---|---|
| 1 | Hydrogen | — | 63 | 52 |
| 2 | Hydrogen + | 9:1 | 72 | 68 |

TABLE 1-continued

| Run No. | Gas used Type | Molar ratio | Yield of indole (%) Reaction mixture A | Reaction mixture B |
|---|---|---|---|---|
| | water vapor | | | |

EXAMPLE 3

The procedure of Example 1 was repeated except that the catalyst of Example 1 was replaced by each of the catalysts indicated in Table 2 and the nitrogen gas was replaced by a mixture of hydrogen gas and water vapor (in a molar ratio of 9:1). The results thus obtained are summarized in Table 2.

TABLE 2

| Run No. | Type of catalyst (weight ratio of carrier components) | Ag content[1] | Specific surface area of carrier (m²/g) | Yield of indole (%) Reaction mixture A | Reaction mixture B |
|---|---|---|---|---|---|
| 3 | Ag/activated carbon | 10 | 620 | 58 | 52 |
| 4 | Ag/SiO₂—ZnO (3:1) | 10 | 210 | 75 | 71 |
| 5 | Ag/SiO₂—ZnO (9:1) | 10 | 330 | 77 | 73 |
| 6 | Ag/SiO₂—ZnO (9:1) | 5 | 330 | 76 | 73 |
| 7 | Ag/SiO₂—ZnO—CaO (83:15:2) | 10 | 205 | 74 | 72 |
| 8 | Ag/SiO₂—ZnO—MgO (83:15:2) | 10 | 215 | 76 | 72 |
| 9 | Ag/SiO₂—MgO (1:1) | 10 | 170 | 64 | 60 |
| 10 | Ag/SiO₂—CaO (1:1) | 10 | 120 | 62 | 59 |
| 11 | Ag/SiO₂—SrO (1:1) | 9 | 150 | 62 | 60 |
| 12 | Ag/δ—Al₂O₃ | 10 | 56 | 38 | 32 |
| 13 | Ag/δ—Al₂O₃ | 8 | 31 | 35 | 30 |

Note:
[1] The amount (in parts by weight) of Ag supported per 100 parts by weight of the carrier.

EXAMPLE 4

Reaction was carried out in the same manner as described in Example 1, except that the ethylene glycol was replaced by propylene glycol or 1,2,4-butanetriol. As a result, skatole and triptophol were obtained in 53% and 13% yields, respectively.

EXAMPLE 5

Reaction was carried out in the same manner as described in Example 1, except that the aniline was replaced by o-toluidine or o-anisidine. As a result, 7-methylindole and 7-methoxyindole were obtained in 32% and 26% yields, respectively.

EXAMPLE 6

Into a 200-ml autoclave made of a titanium alloy and fitted with a stirrer were charged 1 mole of aniline, 0.2 mole of ethylene glycol, and 5 g of an Ag/activated charcoal catalyst (containing 10 parts by weight of Ag per 100 parts by weight of the carrier). After the autoclave was purged with hydrogen gas and filled therewith to a pressure of 5 kg/cm², reaction was carried out at 390° C. for 1 hour with stirring. After completion of the reaction, the catalyst was separated from the reaction mixture by filtration and the resulting reaction product was analyzed by gas chromatography. This revealed that indole was obtained in a 45% yield based on the ethylene glycol.

COMPARATIVE EXAMPLE 1

The procedure of Example 3 was repeated by using a variety of catalysts. The results thus obtained are summarized in Table 3.

TABLE 3

| Run No. | Type of catalyst | Ag content[1] | Specific surface area of carrier ($m^2/g$) | Yield of indole (%) Reaction mixture A | Reaction mixture B |
|---|---|---|---|---|---|
| 10 | Ag [for the synthesis of formalin] | — | — | 0 | 0 |
| 11 | Ag/α-Al$_2$O$_3$ [for the synthesis of ethylene oxide] | 10 | 0.8 | 0 | 0 |
| 12 | SiO$_2$—ZnO (3:1) [carrier of Run No. 4] | — | 210 | 11 | 0 |
| 13 | SiO$_2$—CaO (1:1) [carrier of Run No. 6] | — | 120 | 6 | 0 |
| 14 | Ag/SiO$_2$—ZnO (3:1)[2] | 5 | 9 | 1 | 0 |
| 15 | Ag/α-Al$_2$O$_3$ | 5 | 3 | 0 | 0 |

Note:
[1]The amount (in parts by weight) of Ag supported per 100 parts by weight of the carrier.
[2]This carrier was prepared by carrying out the calcination at 900° C. for 5 hours.

COMPARATIVE EXAMPLE 2

The procedure of Example 3 was repeated except that an Ag catalyst for the synthesis of formalin or an Ag/α-Al$_2$O$_3$ catalyst for the synthesis of ethylene oxide was used and the reaction was carried out at 400° C. With either of the catalysts, no formation of indole was recognized.

COMPARATIVE EXAMPLE 3

The procedure of Example 1 was repeated except that the catalyst of Example 1 or an Ag catalyst for the synthesis of formalin was used and the nitrogen gas was replaced by air. As a result, only tar was produced with no recognizable formation of indole.

COMPARATIVE EXAMPLE 4

The procedure of Example 3 was repeated except that 5 ml of zinc-plated iron pieces (3 mm×3 mm×1 mm) were used as the catalyst and the reaction was carried out at 400° C. As a result, no formation of indole was recognized.

REFERENCE EXAMPLE 1

A stainless steel flow reactor having an internal diameter of 10 mm was packed with 2 ml of each of the catalysts indicated in Table 4. The front end of this reactor was connected to a feed inlet pipe and a gas inlet pipe to establish a feed vaporization zone, while the rear end thereof was connected through an air-cooling zone to a receiver immersed in a dry-ice bath.

A 66.7 wt. % aqueous solution of methanol was introduced into the reactor at a rate of 150 g per hour, and the temperatures of the feed vaporization zone and the reaction zone were kept at 400° C. Then, air was introduced thereinto at a rate of 1.833 Nl per minute, and the temperature of the feed vaporization zone was gradually lowered so that the temperature of the catalyst bed in the reaction zone might be maintained in the range of 600° to 650° C. In a steady state, the temperature of the catalyst bed varied from 600° to 630° C. while that of the feed vaporization zone varied from 150° to 220° C.

The reaction reached a steady state 4 hours after the introduction of the feed material was started. A sample of the condensate was collected for a period between 6 and 7 hours after the introduction of the feed material was started, and analyzed for methanol and formaldehyde by gas chromatography. The results thus obtained are summarized in Table 4.

TABLE 4

| Type of catalyst | Specific surface area of carrier ($m^2/g$) | Ag content[1] | Conversion of MeOH (%) | Yield of CH$_2$O (%) | Selectivity for CH$_2$O (%) |
|---|---|---|---|---|---|
| Ag [for the synthesis of formalin] | — | — | 76 | 54 | 71 |
| Ag/pumice | 6.1 | 10 | 93 | 48 | 52 |
| Ag/SiO$_2$-MgO | 170 | 10 | 100 | 0 | 0 |
| Ag/SiO$_2$-ZnO | 250 | 10 | 100 | 0 | 0 |

Note:
[1]The amount (in parts by weight) of Ag supported per 100 parts by weight of the carrier.

REFERENCE EXAMPLE 2

A reactor similar to that of Example 1 was packed with 5 ml of a catalyst consisting of zinc-plated iron pieces (3 mm×3 mm×1 mm). The internal temperature of the reaction zone was kept at 400° C. and hydrogen gas at atmospheric pressure was passed therethrough at a rate of 10 ml per minute. Then, dehydrogenation reaction was carried out by introducing cyclohexanol thereinto through the feed inlet pipe at a rate of 1.25 ml per minute. A sample of the reaction mixture was collected for a 2-hour period between 1 and 2 hours after the start of the reaction and analyzed by gas chromatography. This revealed that the conversion of cyclohexanol was 32% and the selectivity for cyclohexanone was 84%.

What is claimed is:

1. In a process for the preparation of indoles by reacting an aniline selected from the group consisting of aniline, o-toluidine, m-toluidine, p-toluidine, o-haloaniline, m-haloaniline, p-haloaniline, o-anisidine, m-anisidine and p-anisidine with a 1,2 glycol selected from the group consisting of ethylene glycol, 1,2-propylene glycol and 1,2-butanediol in the presence of a catalyst, the improvement which comprises carrying out the reaction in the presence of a catalyst comprising silver supported on a carrier having a specific surface area of not less than 10 m$^2$/g, said catalyst containing 0.1 to 50 parts by weight of silver per 100 parts by weight of the carrier, and said carrier being SiO$_2$, an oxide mixture of SiO$_2$ and the other metal oxide or oxides or activated carbon.

2. A process as claimed in claim 1 wherein the carrier having a specific surface area of not less than 10 m$^2$/g comprises SiO$_2$; an oxide mixture selected from the group consisting of SiO$_2$-ZnO, SiO$_2$-CdO, SiO$_2$-MgO, SiO$_2$-SrO$_2$, SiO$_2$-In$_2$O$_3$, SiO$_2$-CaO, SiO$_2$-ZnO-CaO, and SiO$_2$-Zno-MgO; or activated carbon.

3. A process as claimed in claim 1 or 4 wherein the weight ratio of SiO$_2$ to the other oxide or oxides in the oxide mixture ranges from 1:0.01 to 1:1.

4. A process as claimed in claim 1 wherein the oxide has a specific surface area of at least 50 m$^2$/g.

5. A process as claimed in claim 1 wherein the reaction is conducted at a temperature of from 200° to 600° C.

6. A process as claimed in claim 5 wherein the reaction is conducted in the presence of hydrogen gas and/or water vapor.

* * * * *